(12) United States Patent  
Bickley et al.

(10) Patent No.: US 9,345,582 B2
(45) Date of Patent: May 24, 2016

(54) METHOD AND APPARATUS FOR RESTORING A SHOULDER JOINT AND/OR ANOTHER JOINT

(71) Applicant: VXP Solutions LLC, Kensington, CT (US)

(72) Inventors: Barry T. Bickley, North Andover, MA (US); Richard E. Zovich, Kensington, CT (US); Aldo M. Zovich, East Hampton, CT (US)

(*) Notice: Subject to any disclaimer, the term of this patent is extended or adjusted under 35 U.S.C. 154(b) by 0 days.

(21) Appl. No.: 14/547,832

(22) Filed: Nov. 19, 2014

(65) Prior Publication Data

US 2015/0142122 A1        May 21, 2015

Related U.S. Application Data

(60) Provisional application No. 61/906,227, filed on Nov. 19, 2013.

(51) Int. Cl.
*A61F 2/40*        (2006.01)
*A61F 2/30*        (2006.01)

(52) U.S. Cl.
CPC .......... *A61F 2/4081* (2013.01); *A61F 2/30734* (2013.01); *A61F 2002/30387* (2013.01); *A61F 2002/30578* (2013.01); *A61F 2002/4085* (2013.01)

(58) Field of Classification Search
CPC ............ A61F 2/34; A61F 2/4081; A61F 2/40
USPC .......................................... 623/19.11, 19.13
See application file for complete search history.

(56) References Cited

U.S. PATENT DOCUMENTS

| 7,753,959 B2 | 7/2010 | Berelsman et al. |
| 2007/0244563 A1 | 10/2007 | Roche et al. |
| 2009/0192621 A1 | 7/2009 | Winslow et al. |
| 2012/0209392 A1 | 8/2012 | Angibaud et al. |
| 2012/0253467 A1 | 10/2012 | Frankle |

*Primary Examiner* — David Isabella
*Assistant Examiner* — Dinah Baria
(74) *Attorney, Agent, or Firm* — Pandiscio & Pandiscio

(57) ABSTRACT

Apparatus for repairing a shoulder joint, including a baseplate having a base portion having a medially-facing surface and a laterally-facing surface, and an opening passing through the medially-facing and laterally-facing surfaces for receiving a screw; and an anterior flange having an anteriorly-facing surface and a posteriorly-facing surface, the anterior flange extending away from, and perpendicular to, the medially-facing surface, the anterior flange having an opening passing through the anteriorly-facing and posteriorly-facing surfaces for accepting a screw; an articulating surface component for mounting to the laterally-facing surface for covering the laterally-facing surface; and an anterior cover for mounting to the anteriorly-facing surface and configured to lock the articulating surface component to the base portion, such that when the anterior cover is mounted to the anterior flange, the articulating surface component is locked to the base portion.

20 Claims, 14 Drawing Sheets

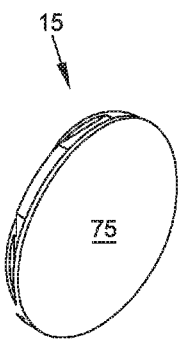
FIG. 12
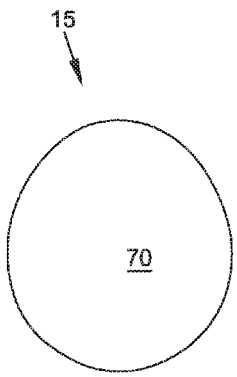
FIG. 13
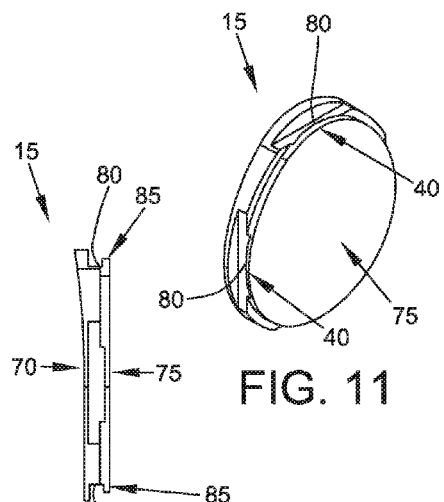
FIG. 14
FIG. 11

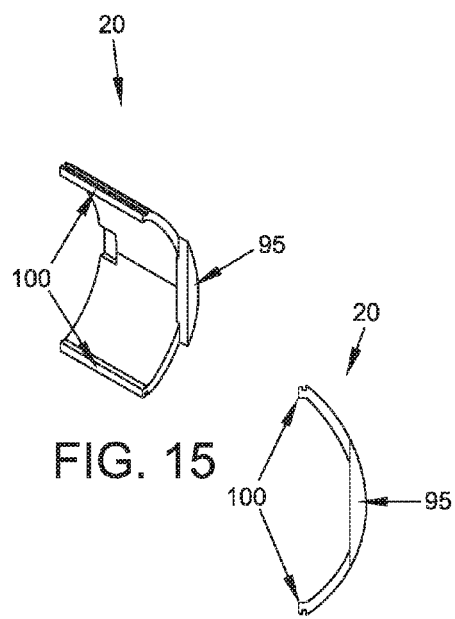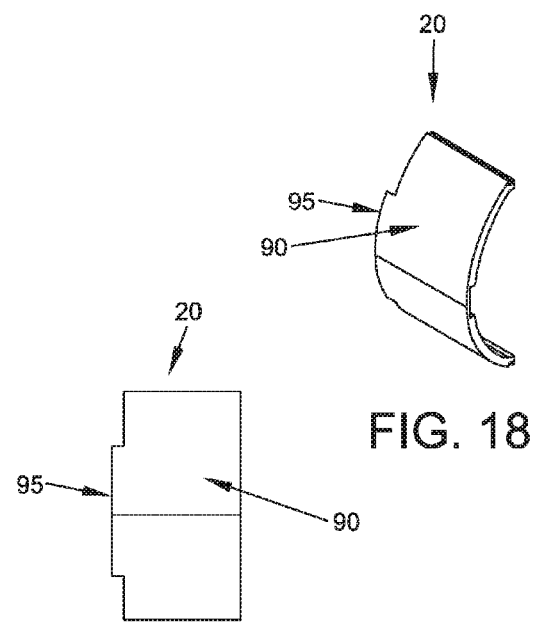

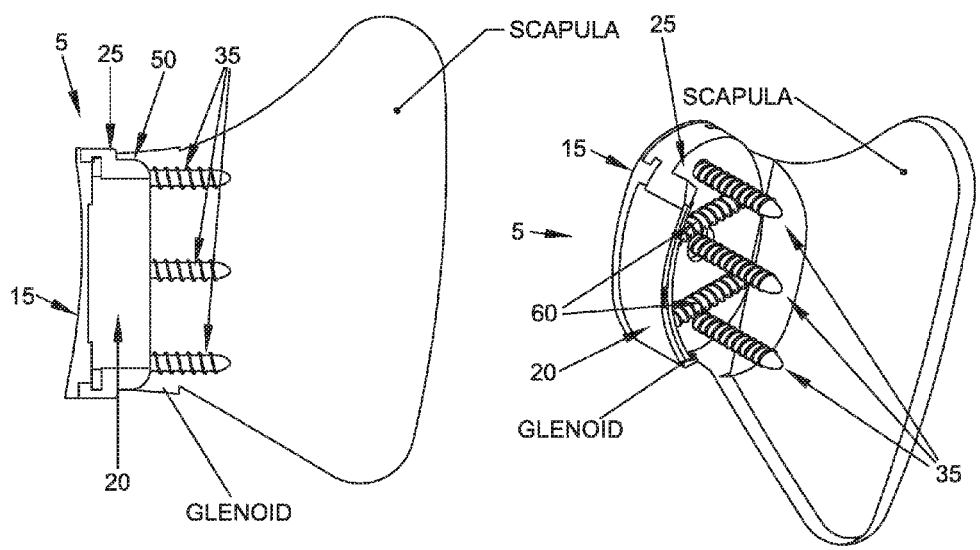

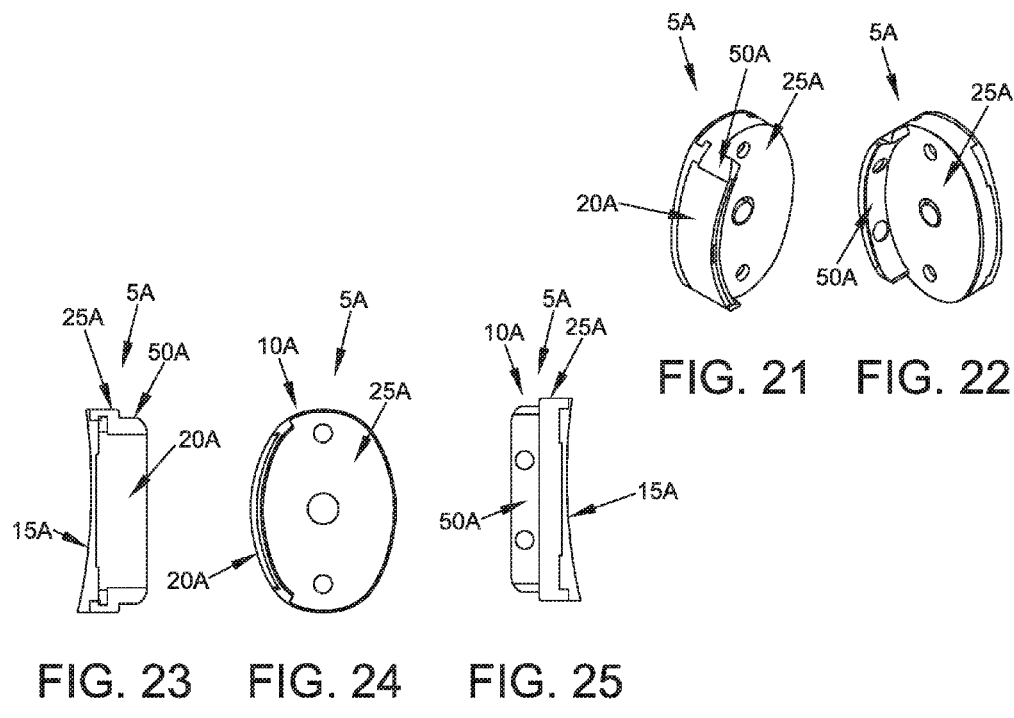

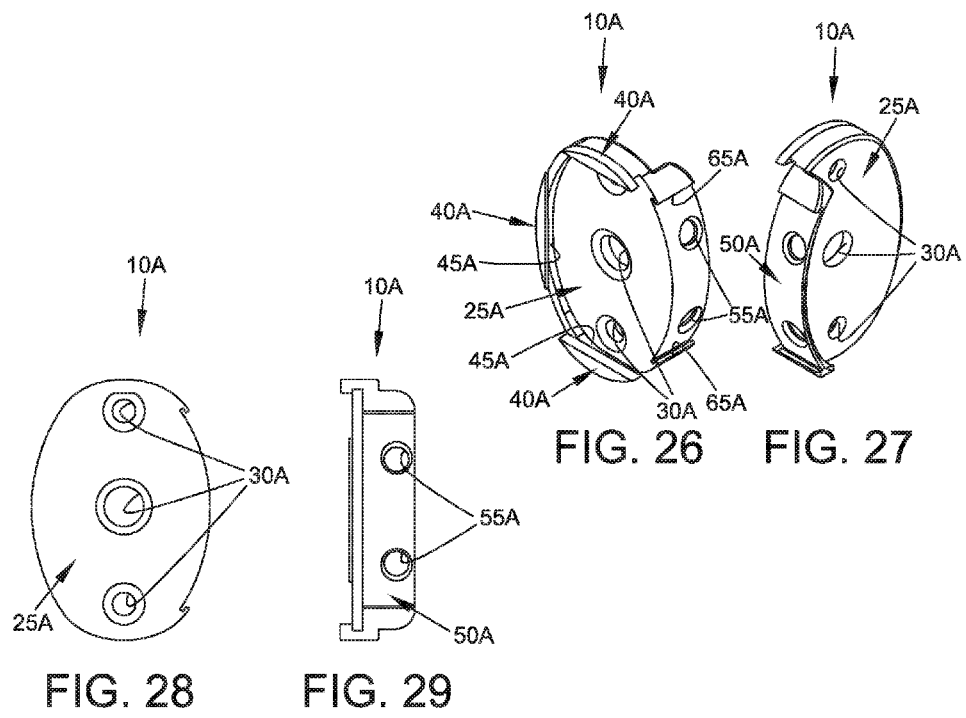

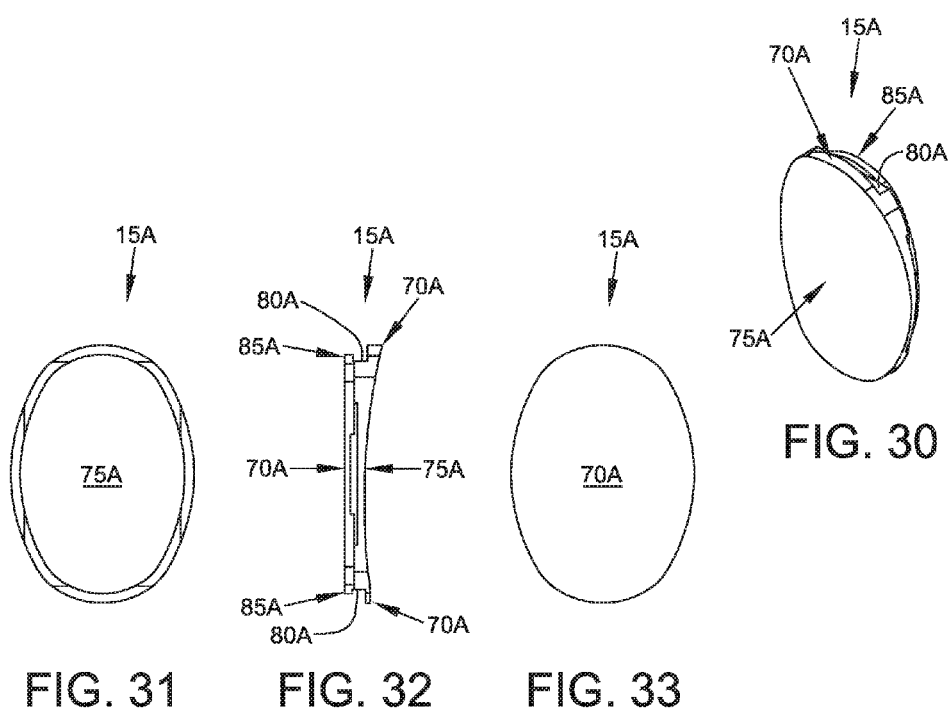

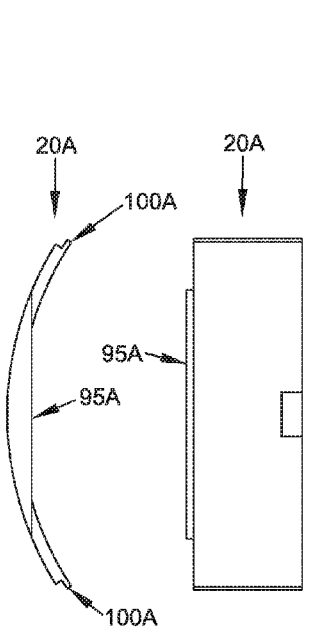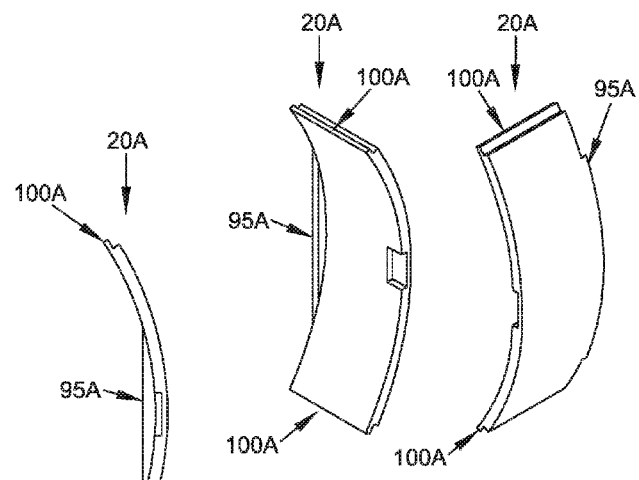
FIG. 34  FIG. 35
FIG. 36  FIG. 37  FIG. 38

METHOD AND APPARATUS FOR RESTORING A SHOULDER JOINT AND/OR ANOTHER JOINT

REFERENCE TO PENDING PRIOR PATENT APPLICATION

This patent application claims benefit of prior U.S. Provisional Patent Application Ser. No. 61/906,227, filed Nov. 19, 2013 by Barry T. Bickley et al. for METHOD AND APPARATUS FOR RESTORING A SHOULDER JOINT, which patent application is hereby incorporated herein by reference.

FIELD OF THE INVENTION

This invention relates to medical procedures and apparatus in general, and more particularly to medical procedures and apparatus for restoring a shoulder joint and/or another joint.

BACKGROUND OF THE INVENTION

The shoulder joint is formed at the convergence of the proximal humerus and the glenoid. More particularly, and looking now at FIGS. 1-3, the proximal humerus comprises a protrusion (or "head"), and the lateral glenoid comprises a recess (or "socket") for receiving the protrusion (or head) of the proximal humerus. Soft tissue (e.g., ligaments, tendons, muscles, etc.) stabilize the joint and permit the proximal humerus to articulate through a range of motion with respect to the glenoid.

Shoulder joint replacement surgery seeks to replace one or more of the operative elements of the shoulder joint with prosthetic components so as to provide long-lasting function and pain-free mobility. By way of example but not limitation, in a "standard" shoulder joint replacement surgery, the proximal humerus may be replaced by a prosthetic ball-and-stem, the lateral glenoid may be replaced by a prosthetic socket, or both. By way of further example but not limitation, in a "reverse" shoulder joint replacement surgery, the proximal humerus may be provided with a prosthetic socket and the lateral glenoid may be provided with a prosthetic protrusion.

SUMMARY OF THE INVENTION

The present invention is directed to situations where the lateral glenoid is to be replaced by a prosthesis.

In one form of the invention, the glenoid prosthesis comprises a socket which mimics the natural socket of the glenoid.

In another form of the invention, the glenoid prosthesis comprises a protrusion for interaction with a prosthetic socket formed in the lateral humerus, in a so-called "reverse" shoulder replacement.

Significantly, the glenoid prosthesis is constructed so as to allow a surgeon to switch from a standard shoulder replacement procedure to a reverse shoulder replacement procedure, or vice-versa, either during surgery or at a later date.

While the present invention is specifically intended for use in the glenoid, the prosthesis of the present invention may also be adapted for use in a variety of other joints within the body, e.g., the hip, knee, elbow, wrist, ankle, etc.

In one preferred form of the invention, there is provided apparatus for repairing a shoulder joint, said apparatus comprising:

a baseplate for mounting to a glenoid, said baseplate comprising:

a base portion comprising a medially-facing surface and a laterally-facing surface, and at least one opening passing through said medially-facing surface and said laterally-facing surface for receiving at least one base portion screw; and an anterior flange carried by said base portion, said anterior flange comprising an anteriorly-facing surface and a posteriorly-facing surface, said anterior flange extending away from, and perpendicular to, said medially-facing surface of said base portion, said anterior flange further comprising at least one opening passing through said anteriorly-facing surface and said posteriorly-facing surface for accepting at least one flange screw;

an articulating surface component for mounting to said laterally-facing surface of said base portion so as to substantially cover said laterally-facing surface of said base portion; and an anterior cover for mounting to said anteriorly-facing surface of said anterior flange;

wherein said anterior cover is configured to lock said articulating surface component to said base portion, such that when said anterior cover is mounted to said anterior flange, said articulating surface component is locked to said base portion.

In another preferred form of the invention, there is provided a method for restoring a shoulder joint, said method comprising:

providing apparatus for repairing a shoulder joint, said apparatus comprising:

a baseplate for mounting to a glenoid, said baseplate comprising:

a base portion comprising a medially-facing surface and a laterally-facing surface, and at least one opening passing through said medially-facing surface and said laterally-facing surface for receiving at least one base portion screw; and an anterior flange carried by said base portion, said anterior flange comprising an anteriorly-facing surface and a posteriorly-facing surface, said anterior flange extending away from, and perpendicular to, said medially-facing surface of said base portion, said anterior flange further comprising at least one opening passing through said anteriorly-facing surface and said posteriorly-facing surface for accepting at least one flange screw;

an articulating surface component for mounting to said laterally-facing surface of said base portion so as to substantially cover said laterally-facing surface of said base portion; and an anterior cover for mounting to said anteriorly-facing surface of said anterior flange;

wherein said anterior cover is configured to lock said articulating surface component to said base portion, such that when said anterior cover is mounted to said anterior flange, said articulating surface component is locked to said base portion;

mounting said baseplate to the glenoid by positioning said baseplate against the glenoid and passing at least one base portion screw through said at least one opening in said base portion, and by passing at least one flange screw through said at least one opening in said flange;

mounting said articulating surface component to said base portion, such that said at least one base portion screw is covered by said articulating surface component; and mounting said anterior cover to said anterior flange, such that said articulating surface component is locked to said base portion and said at least one flange screw is covered by said anterior cover.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 11-14 are schematic views of the articulating surface component of the novel glenoid prosthesis shown in FIGS. 4-7;

FIGS. 15-18 are schematic views of the anterior cover of the novel glenoid prosthesis shown in FIGS. 4-7;

FIGS. 19 and 20 are schematic views showing the novel glenoid prosthesis of FIGS. 4-7 secured in position to a resected glenoid;

FIGS. 21-38 are schematic views showing another novel glenoid prosthesis formed in accordance with the present invention.

DETAILED DESCRIPTION OF THE PREFERRED EMBODIMENTS

The present invention comprises a new shoulder joint prosthesis for replacing the lateral glenoid.

In one form of the invention, the glenoid prosthesis comprises a socket which mimics the natural socket of the glenoid.

In another form of the invention, the glenoid prosthesis comprises a protrusion for interaction with a prosthetic socket formed in the lateral humerus, in a so-called "reverse" shoulder replacement.

Significantly, the glenoid prosthesis is constructed so as to allow a surgeon to switch from a standard shoulder replacement procedure to a reverse shoulder replacement procedure, or vice-versa, either during surgery or at a later date.

In order to simplify description of the present invention, the new glenoid prosthesis will first be discussed in the context of providing a socket which mimics the natural socket of the glenoid. Thereafter, the new glenoid prosthesis will be discussed in the context of providing a protrusion for interaction with a prosthetic socket formed in the lateral humerus, in a so-called "reverse" shoulder replacement.

Glenoid Prosthesis Comprising a Socket which Mimics the Natural Socket of the Glenoid Looking first at FIGS. 4-7, there is shown a novel glenoid prosthesis 5 formed in accordance with the present invention. Glenoid prosthesis 5 generally comprises a baseplate 10, an articulating surface component 15 and an anterior cover 20.

Figure 1:
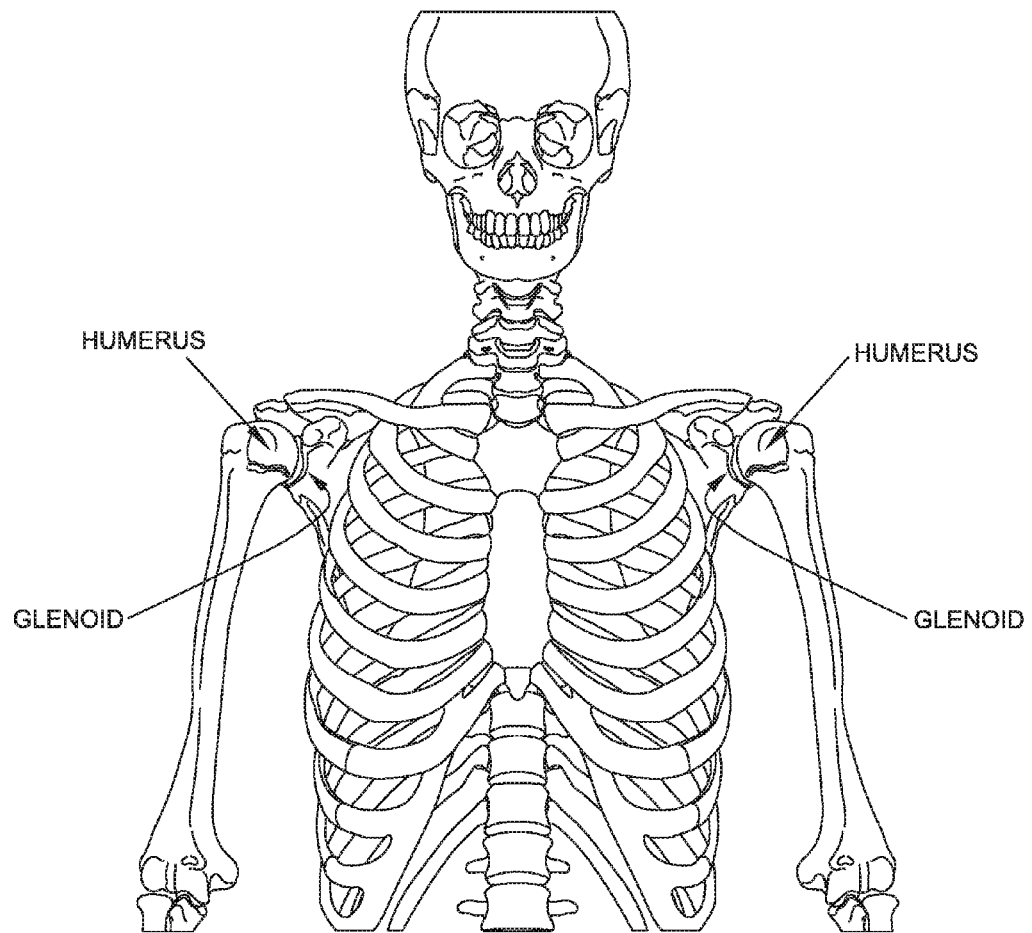
FIG. 1 is a schematic view showing the skeletal structure of the upper half of a human torso.
Figure 2:
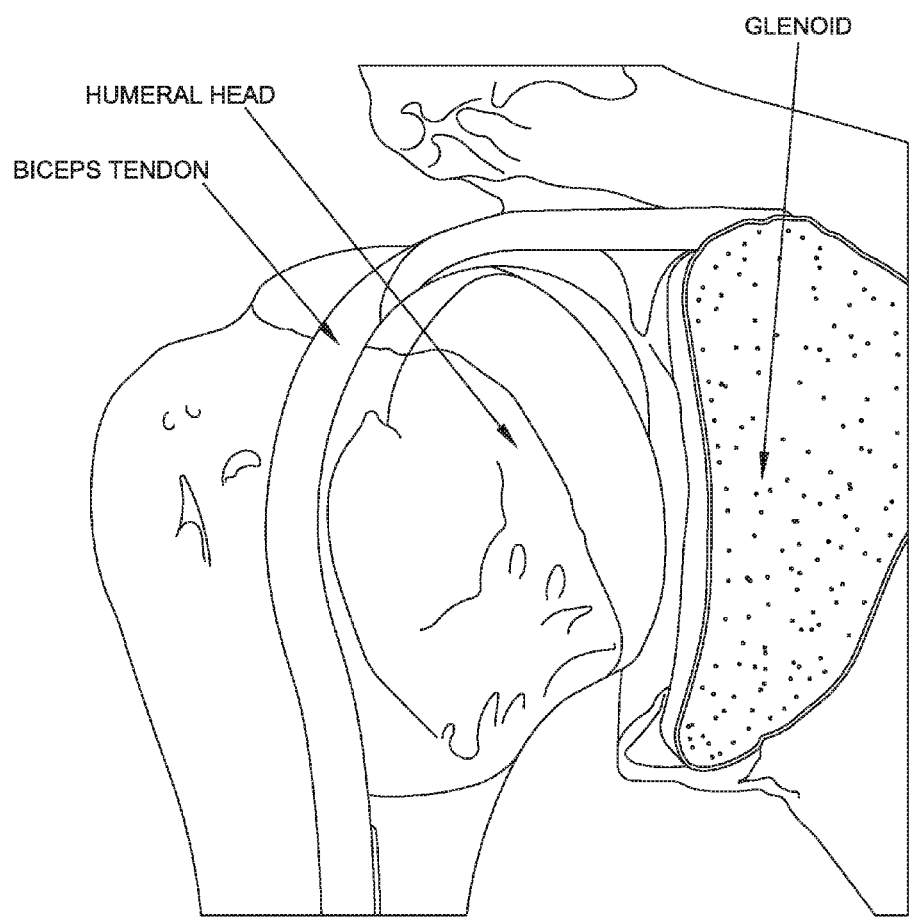
FIG. 2 is a schematic view showing a right shoulder joint.
Figure 3:
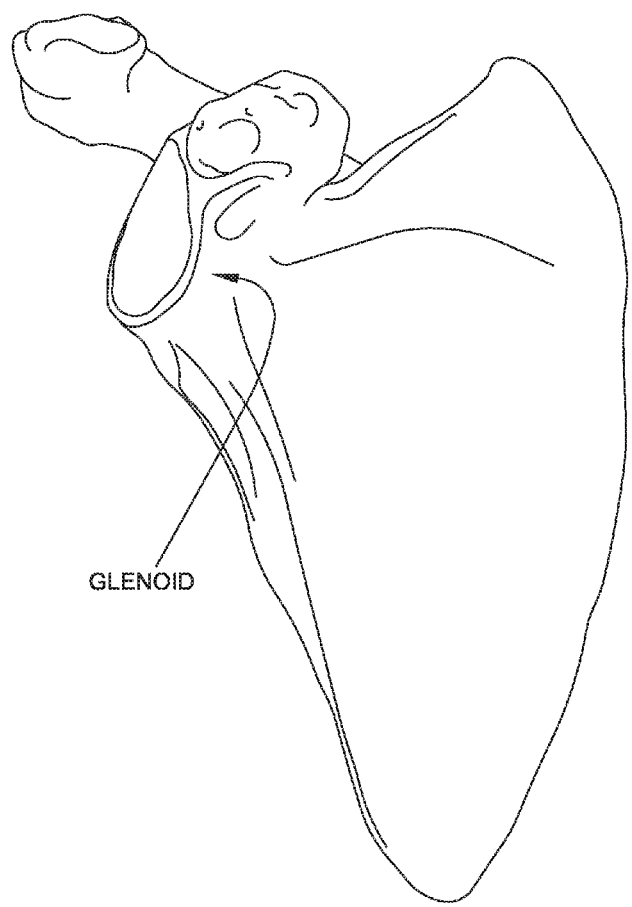
FIG. 3 is a schematic view showing a right glenoid.
Figure 4:
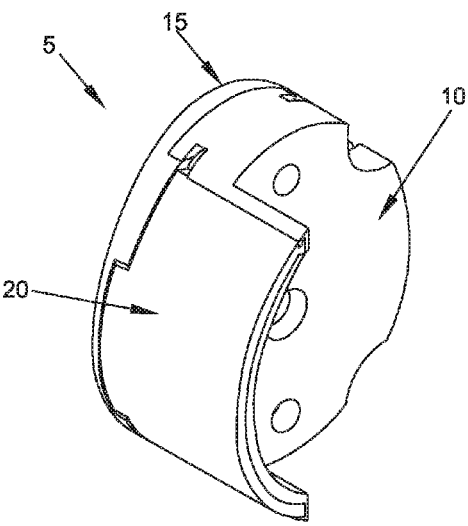
FIGS. 4-7 are schematic views showing a novel glenoid prosthesis formed in accordance with the present invention.
Figure 5:
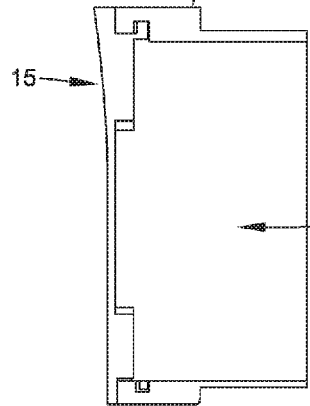
Figure 6:
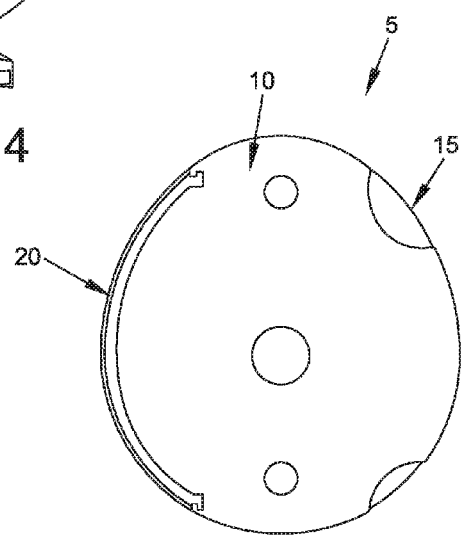
Figure 7:
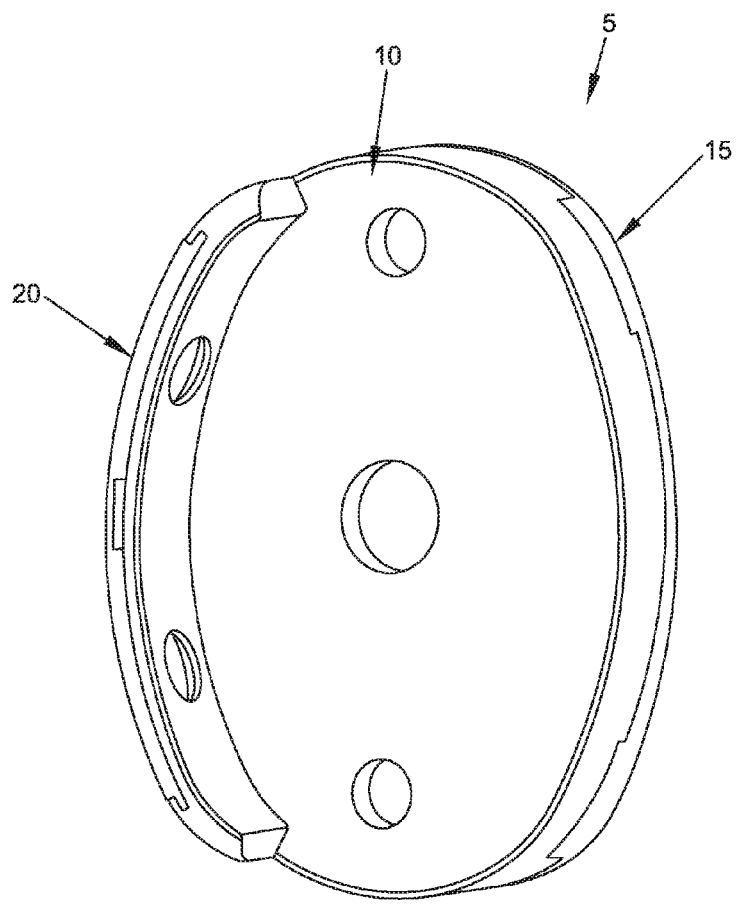
Figure 9:
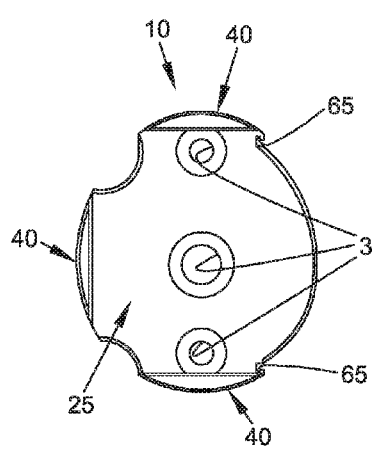
FIGS. 8-10 are schematic views showing the baseplate of the novel glenoid prosthesis shown in FIGS. 4-7.
Figure 10:
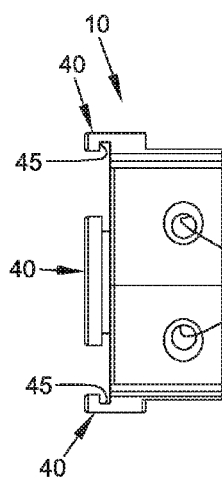
Figure 8:
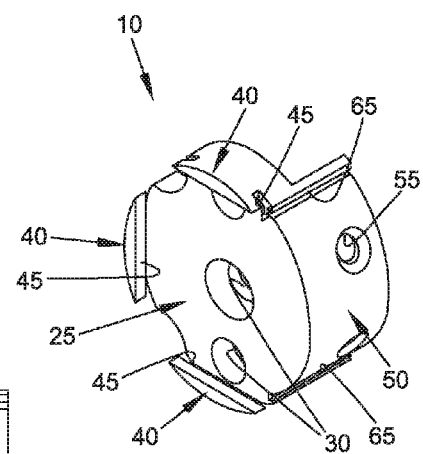

More particularly and looking now at FIGS. 8-10, baseplate 10 comprises a substantially flat base portion 25 for seating against the surface of the resected glenoid. Base portion 25 comprises a plurality of holes 30 passing therethrough for receiving bone screws 35 therein (see FIGS. 19 and 20), whereby to secure base portion 25 (and hence baseplate 10) to the surface of the resected glenoid, as will hereinafter be discussed. Baseplate 10 further comprises a plurality of protrusions 40 extending outwardly from base portion 25 of baseplate 10, wherein each protrusion 40 comprises a groove 45 for securing articulating surface component 15 to baseplate 10, as will hereinafter be discussed. An anterior flange 50 extends medially and substantially perpendicular to the plane of base portion 25. Anterior flange 50 comprises a plurality of holes 55 passing therethrough for receiving bone screws 60 therein (FIG. 20), whereby to secure anterior flange 50 (and hence baseplate 10) to the surface of the resected glenoid, as will also hereinafter be discussed. Anterior flange 50 further comprises a plurality of grooves 65 for securing anterior cover 20 to baseplate 10, as will hereinafter be discussed.

Looking next at FIGS. 11-14, articulating surface component 15 comprises a concave laterally-facing surface 70 and a planar medially-facing surface 75. A plurality of grooves 80 are disposed around the perimeter of articulating surface component 15 intermediate laterally-facing surface 70 and medially-facing surface 75, whereby to form a plurality of tabs 85 out of portions of the perimeter of medially-facing surface 75. Tabs 85 are sized to be received in grooves 45 of baseplate 10, whereby to secure articulating surface component 15 to baseplate 10 (e.g., by a friction fit, a snap fit, etc.). By way of example but not limitation, articulating surface component 15 may be formed out of polyethylene so as to provide a smooth articulating surface. Concave laterally-facing surface 70 preferably has a surface profile approximating the surface profile of the native lateral glenoid.

Looking next at FIGS. 15-18, anterior cover 20 comprises a smooth anteriorly-facing surface 90, a protrusion 95 located along one side of anterior cover 20, and two tabs 100 sized to be slidably received in slots 65 of anterior flange 50 of baseplate 10.

In use, the native bone (i.e., the native lateral glenoid) is first surgically resected so as to provide a seat for receiving glenoid prosthesis 5 (i.e., the lateral glenoid is resected so as to provide a surface for seating base portion 25 and flange 50 of baseplate 10 against the bone). Then baseplate 10 is positioned against the resected lateral glenoid, and a plurality of bone screws 35 are advanced through holes 30 of base portion 25 into the resected lateral glenoid, whereby to secure base portion 25 to the resected bone (FIGS. 19 and 20). Next, a plurality of bone screws 60 are advanced through holes 55 of flange 50 into the lateral glenoid (FIG. 20), whereby to secure flange 50 to the resected lateral glenoid. It should be appreciated that by having bone screws 60 disposed substantially perpendicular to bone screws 35, baseplate 10 of glenoid prosthesis 5 is securely fastened to the native bone via a multi-planar fixation.

Next, articulating surface component 15 is secured to baseplate 10 by sliding tabs 85 of articulating surface component 15 into grooves 45 of baseplate 10. Note that articulating surface component 15 overlies bone screws 35, thereby preventing bone screws 35 from backing out of the resected lateral glenoid.

Finally, anterior cover 20 is secured to anterior flange 50 (and hence, to baseplate 10) by sliding tabs 100 of anterior cover 20 into grooves 65 of anterior flange 50 until protrusion 95 of anterior cover 20 engages the perimeter of medially-facing surface 75 of articulating surface component 15. Note that anterior cover 20 overlies bone screws 60, thereby preventing bone screws 60 from backing out of the resected lateral glenoid. It should be appreciated that after anterior cover 20 is secured to baseplate 10 in this fashion, anterior cover 20 "locks" articulating surface component 15 to baseplate 10, thereby preventing articulating surface component 15 from being removed from baseplate 10 without first removing anterior cover 20.

Note that novel glenoid prosthesis 5 is "universal", in the sense that the same glenoid prosthesis may be used to reconstruct either the right shoulder of the patient or the left shoulder of the patient. Thus, while the glenoid prosthesis 5 shown in FIGS. 4-18 is shown oriented for a right shoulder reconstruction, and while the glenoid prosthesis 5 is shown in FIGS. 19 and 20 as being used in a right shoulder reconstruction, the same glenoid prosthesis 5 may be used for a left shoulder reconstruction, i.e., by simply rotating the orientation of the glenoid prosthesis 5 by 180 degrees.

FIGS. 21-38 show another novel glenoid prosthesis 5A formed in accordance with the present invention. The novel glenoid prosthesis 5A shown in FIGS. 21-38 is generally similar to the novel glenoid prosthesis 5 shown in FIGS. 4-20, except that the geometry and/or size of several of the elements comprising novel glenoid prosthesis 5A vary from the geometry and/or size of their counterpart elements comprising novel glenoid prosthesis 5. It will be appreciated that FIGS. 21-25 show novel glenoid prosthesis 5A in its assembled form; FIGS. 26-29 show baseplate 10A of novel glenoid prosthesis 5A; FIGS. 30-33 show articulating surface component 15A of novel glenoid prosthesis 5A; and FIGS. 34-38 show anterior cover 20A of novel glenoid prosthesis 5A.

Figure 39:
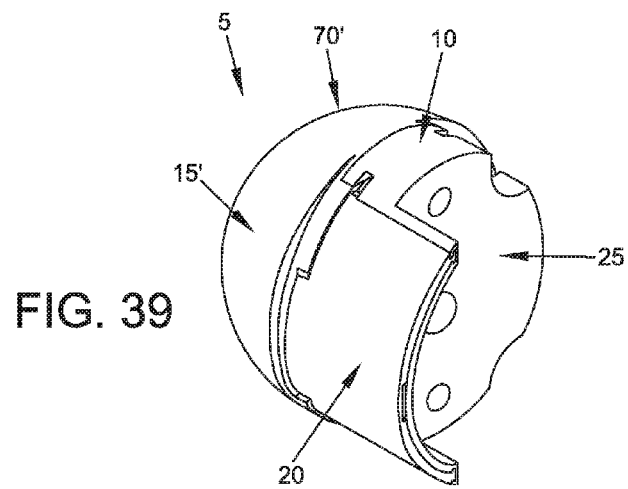
FIGS. 39-41 are schematic views showing a glenoid prosthesis which may be used in a so-called "reverse" shoulder replacement surgery.
Figure 40:
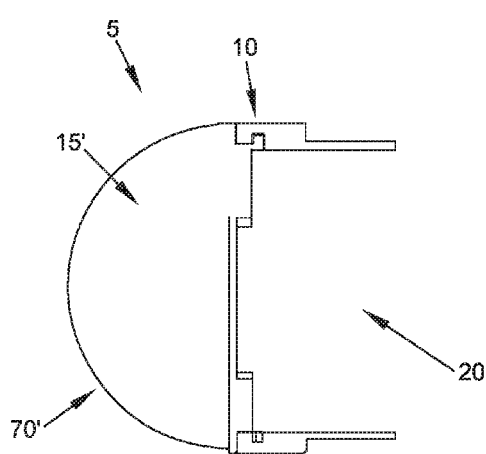
Figure 41:
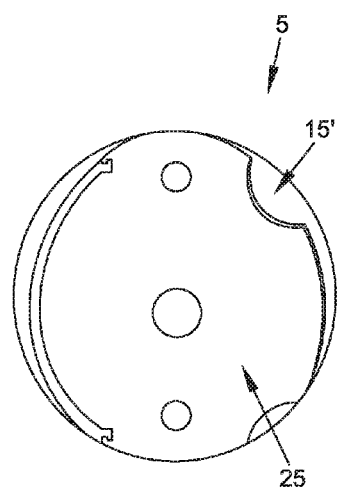

Glenoid Prosthesis Comprising a Protrusion for Interaction with a Prosthetic Socket Formed in the Lateral Humerus In the foregoing description, glenoid prosthesis 5 is discussed in the context of providing a concave articulating surface to approximate the socket geometry of the native glenoid. However, it should also be appreciated that, if desired, articulating surface component 15 can comprise a substantially convex laterally-facing surface (i.e., a protruding element), rather than the aforementioned concave laterally-facing surface 70 (or concave laterally-facing surface 70A), whereby to provide a so-called "reverse" shoulder replacement prosthesis. By way of example but not limitation, and looking now at FIGS. 39-41, glenoid prosthesis 5 may comprise an articulating surface component 15' having a convex laterally-facing surface 70', whereby to provide the "protrusion" portion of the shoulder joint (rather than the "socket" portion of the shoulder joint) and which can engage the "socket" portion of another bone structure or another prosthesis so as to provide an articulating joint.

Some Significant Aspects of the Invention

Significantly, as discussed above, the glenoid prosthesis of the present invention provides a baseplate that can be used as a foundation for either a "standard" shoulder replacement procedure or a "reverse" shoulder replacement procedure. The glenoid prosthesis of the present invention allows a surgeon to easily switch from one procedure to the other procedure (i.e., from a "standard" shoulder replacement procedure to a "reverse" shoulder replacement procedure, or vice-versa) either intra-operatively or at a later date, if it is decided that one or the other procedure is more appropriate, such as in the scenario where a patient has a standard prosthesis placed for arthritis but, at a later date, develops a rotator cuff tear and there is a need to revise the standard prosthesis to a reverse shoulder replacement so as to improve his/her function. In such a case, with the present invention, the surgeon can simply exchange the articulating surface component 15 that is fitted to the baseplate 10 and not have to revise the entire glenoid component, which could potentially jeopardize the somewhat limited bone stock at the natural glenoid on the scapula. In other words, where it is desired to revise the standard prosthesis to a reverse prosthesis, the surgeon can simply exchange the standard articulating surface component 15 (having a concave laterally-facing surface 70) with the reverse articulating surface component 15' (having a convex laterally-facing surface 70') without ever having to remove baseplate 10 from the resected glenoid.

Securing a glenoid prosthesis to the native lateral glenoid so as to avoid loosening, given the shape and size of the bone structure, is a well-known problem for surgeons. Baseplate 10 of the present invention is mounted to the glenoid by first preparing a bone surface (i.e., by resecting the lateral glenoid) so as to accommodate baseplate 10 of glenoid prosthesis 5 (or baseplate 10A of glenoid prosthesis 5A). Baseplate 10 of glenoid prosthesis 5 (or baseplate 10A of glenoid prosthesis 5A) is then mounted to the resected glenoid and secured in place by screws 35 (or pins) that go through baseplate 10 (or baseplate 10A) perpendicular to the face of the resected lateral glenoid. However, a unique feature in the glenoid prosthesis of the present invention is the provision of additional screw fixation that is placed from the anterior aspect of the baseplate, i.e., through anterior flange 50 (or anterior flange 50A). These screws (i.e., screws 60) go into the native glenoid at an angle and provide fixation from a different plane than the screws (i.e., screws 35) going perpendicular to the plane of the glenoid face. This multi-planar fixation of baseplate 10 (or baseplate 10A) is different than the standard method of glenoid fixation and provides greater strength and durability to the glenoid prosthesis. No other glenoid prosthesis provides this feature.

Screws 35 passing through substantially flat base portion 25 of baseplate 10 (or through substantially flat base portion 25A of baseplate 10A), and/or screws 60 passing through anterior flange 50 of baseplate 10 (or flange 50A of baseplate 10A), can be locking, i.e., screws 35 can tighten into threaded holes 30 in baseplate 10 (or threaded holes 30A in baseplate 10A) that correspond to threads on the screw head, so as to couple the screws and baseplate together), and/or screws 60 can tighten into threaded holes 55 in anterior flange 50 (or threaded holes 55A in anterior flange 50A) so as to couple the screws and anterior flange together. Or screws 35 and/or screws 60 can be non-locking, i.e., traditional smooth-headed screws 35 that go through the baseplate 10 (or baseplate 10A) but do not mechanically lock the screws to the baseplate, and/or traditional smooth-headed screws 60 that go through anterior flange 50 (or anterior flange 50A) but do not mechanically lock the screws to the anterior flange.

Additionally, one or more of holes 30 in baseplate 10 (or holes 30A in baseplate 10A) can be replaced by slots. These slots can allow greater options in placing screws 35. If desired, these slots may have offset edges that act as a thread that corresponds to a thread on the screw head, so as to provide a mechanical lock between screws 35 and baseplate 10. Furthermore, one or more of holes 55 in anterior flange 50 (or holes 55A in anterior flange 50A) can be replaced by slots. These slots can allow greater options in placing screws 60. If desired, these slots may have offset edges that act as a thread that corresponds to a thread on the screw head, so as to provide a mechanical lock between screws 60 and anterior flange 50.

As noted above, screws 35 on the face of baseplate 10 (or baseplate 10A) are prevented from backing out by the articulating surface component 15 (or by the articulating surface component 15A, or by the articulating surface component 15') that is mounted to baseplate 10 (or baseplate 10A).

As also noted above, screws 60 extending through anterior flange 50 (or anterior flange 50A) are covered by a separate cover plate (i.e., anterior cover 20 or anterior cover 20A) that acts as a "door" to allow the standard articulating surface component 50 (or articulating surface component 50A), or the reverse articulating surface component 50', to be slid into baseplate 10 (or baseplate 10A). Note that as the articulating surface component is slid into place on the baseplate, the articulating surface component is caught by grooves 45 on baseplate 10 (or grooves 45A on baseplate 10A) so that the articulating surface component cannot move in a plane perpendicular to the face of the baseplate. Note also that the articulating surface component will be unable to move anterior/posterior, inasmuch as the articulating surface component is bound posteriorly by a protrusion 40 of baseplate 10 (or a protrusion 40A of baseplate 10A) and anteriorly by the anterior cover (which is mounted in place after positioning of the articulating surface component). With the desired articulating surface component slid into place on the baseplate, the final step is to slide the anterior cover along the anterior flange of the baseplate, in the grooves in the anterior flange that accommodate the anterior cover. The anterior cover will catch on the baseplate and/or the articulating surface component when the anterior cover is fully seated, thereby providing a snap fit. There is no force on the anterior cover to back out, as there is no movement of the articulating surface component on the baseplate in the plane perpendicular to the face of the implant, and the anterior cover is further secured by catching on the articulating surface component and grooves on the baseplate. The anterior cover also covers the anterior screws (i.e., screws 60) so they cannot loosen and back out and, in effect, this construct locks all the components together as one unit so as to minimize the risk of the entire glenoid baseplate loosening over time.

It should be appreciated that if the articulating surface component should become worn and require replacement, the articulating surface component can be replaced without dismounting the baseplate from the resected glenoid, thereby preserving the fusion which has been established between the baseplate and the bone. More particularly, where the articulating surface component has become worn and requires replacement, the anterior cover is removed, the worn articulating surface component is dismounted from the baseplate, the new articulating surface component is installed on the baseplate, and then the anterior cover is replaced.

If it is desired to revise the prosthesis, e.g., to convert the glenoid prosthesis from a socket-type prosthesis to a protrusion-type prosthesis, the anterior cover 20 (or the anterior cover 20A) can easily be removed as the catching mechanism (i.e., the snap fit of the anterior cover with the articulating surface component) is easily overcome by inserting a separate flat tool (such as a flat screw driver, not shown) in the groove at the lateral-most aspect of the anterior cover, and then twisting the tool. This action slides the anterior cover medially in the grooves 65 (or grooves 65A) that the anterior cover sits in, and begins the disassembly process. With the anterior cover removed, the articulating surface component on the base plate can then be slid out anteriorly and exchanged for a reverse (dome-shaped) articulating surface component (i.e., articulating surface component 15'), allowing for easy revision to a reverse prosthesis. The reverse (dome-shaped) articulating surface component 15' is then secured in place by replacing the anterior cover, whereupon the revision is complete, without ever needing to affect the security and fixation of the baseplate to the resected lateral glenoid.

If it is desired to remove the entire glenoid prosthesis, e.g., such as in the case of a significant infection, then the components are disassembled in a similar fashion. The anterior cover is removed, which exposes the anterior screws 60 and allows for removal of the articulating surface component from the baseplate. Removal of the articulating surface component exposes the screws 35 extending through the baseplate. All screws can then be removed, with no scar or fibrous ingrowth in the screw heads inasmuch as the screw heads have been covered previously during the life of the implant.

Thus it will be seen that the novel glenoid prosthesis of the present invention allows the surgeon to mount a baseplate to the resected glenoid, and then add components to the baseplate, so that a worn component of the system can be easily replaced, or the shoulder reconstruction can be easily revised from standard reconstruction to a reverse reconstruction, without ever disrupting attachment of the baseplate to the resected glenoid.

It will also be seen that the novel glenoid prosthesis provides a unique multi-planar fixation feature to the baseplate, so as to allow better fixation of the glenoid prosthesis to the resected glenoid.

And it will be seen that the manner in which the various components of the novel glenoid prosthesis fit together ensures that when they are assembled, the components together prevent any of the individual components from loosening or coming apart. However, when desired, a portion of the construct can be disassembled so as to allow replacement of the articulating surface component (either because the articulating surface component has become worn, or because the shoulder reconstruction is to be revised from a standard glenoid insert to a reverse glenosphere insert); or the construct can be completely disassembled and removed if needed, e.g., such as in the case of a significant infection.

Applicable Joints

While the present invention is specifically intended for use in the glenoid, it will be appreciated that the prosthesis of the present invention may be adapted for use in a variety of other joints within the body, e.g., the hip, knee, elbow, wrist, ankle, etc. In this respect it should be appreciated that inasmuch as the articulating surface component of the new prosthesis can have various profiles according to the articulating surface it is to replace, the prosthesis can be used in a wide range of joint reconstructions.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for repairing a shoulder joint, said apparatus comprising:
   a baseplate for mounting to a glenoid, said baseplate comprising:

a base portion comprising a medially-facing surface and a laterally-facing surface, and at least one opening passing through said medially-facing surface and said laterally-facing surface for receiving at least one base portion screw; and an anterior flange carried by said base portion, said anterior flange comprising an anteriorly-facing surface and a posteriorly-facing surface, said anterior flange extending away from, and perpendicular to, said medially-facing surface of said base portion, said anterior flange further comprising at least one opening passing through said anteriorly-facing surface and said posteriorly-facing surface for accepting at least one flange screw;

an articulating surface component for mounting to said laterally-facing surface of said base portion so as to substantially cover said laterally-facing surface of said base portion; and an anterior cover for mounting to said anteriorly-facing surface of said anterior flange;

wherein said anterior cover is configured to lock said articulating surface component to said base portion, such that when said anterior cover is mounted to said anterior flange, said articulating surface component is locked to said base portion.

2. Apparatus according to claim 1 wherein said base portion further comprises a plurality of protrusions extending perpendicular to said laterally-facing surface, such that said plurality of protrusions defines a plurality of grooves, and further wherein said articulating surface component comprises a plurality of tabs disposed around the perimeter of said articulating surface component, said plurality of tabs being sized to be received in said plurality of grooves of said base portion.

3. Apparatus according to claim 2 wherein said anteriorly-facing surface of said anterior flange comprises at least one groove, and further wherein said anterior cover comprises at least one tab sized to be received in said at least one groove of said anterior flange.

4. Apparatus according to claim 3 wherein said anterior cover further comprises a lateral protrusion extending laterally from the lateralmost edge of said anterior cover.

5. Apparatus according to claim 4 wherein said lateral protrusion of said anterior cover engages the perimeter of said articulating surface component when said articulating surface component is mounted to said base portion, whereby to lock said articulating surface component to said base portion.

6. Apparatus according to claim 1 wherein said baseplate is secured to the glenoid by at least one base portion screw disposed in said at least one opening in said base portion and by at least one flange screw disposed in said at least one opening in said flange.

7. Apparatus according to claim 1 wherein said laterally-facing surface of said articulating surface component is concave.

8. Apparatus according to claim 1 wherein said laterally-facing surface of said articulating surface component is convex.

9. A method for restoring a shoulder joint, said method comprising:
providing apparatus for repairing a shoulder joint, said apparatus comprising:
a baseplate for mounting to a glenoid, said baseplate comprising:
a base portion comprising a medially-facing surface and a laterally-facing surface, and at least one opening passing through said medially-facing surface and said laterally-facing surface for receiving at least one base portion screw; and an anterior flange carried by said base portion, said anterior flange comprising an anteriorly-facing surface and a posteriorly-facing surface, said anterior flange extending away from, and perpendicular to, said medially-facing surface of said base portion, said anterior flange further comprising at least one opening passing through said anteriorly-facing surface and said posteriorly-facing surface for accepting at least one flange screw;

an articulating surface component for mounting to said laterally-facing surface of said base portion so as to substantially cover said laterally-facing surface of said base portion; and an anterior cover for mounting to said anteriorly-facing surface of said anterior flange;

wherein said anterior cover is configured to lock said articulating surface component to said base portion, such that when said anterior cover is mounted to said anterior flange, said articulating surface component is locked to said base portion;

mounting said baseplate to the glenoid by positioning said baseplate against the glenoid and passing at least one base portion screw through said at least one opening in said base portion, and by passing at least one flange screw through said at least one opening in said flange;

mounting said articulating surface component to said base portion, such that said at least one base portion screw is covered by said articulating surface component; and mounting said anterior cover to said anterior flange, such that said articulating surface component is locked to said base portion and said at least one flange screw is covered by said anterior cover.

10. A method according to claim 9 wherein the glenoid is resected prior to mounting said baseplate to the glenoid.

11. A method according to claim 9 wherein said base portion further comprises a plurality of protrusions extending perpendicular to said laterally-facing surface, such that said plurality of protrusions defines a plurality of grooves, and further wherein said articulating surface component comprises a plurality of tabs disposed around the perimeter of said articulating surface component, said plurality of tabs being sized to be received in said plurality of grooves of said base portion.

12. A method according to claim 11 wherein said anteriorly-facing surface of said anterior flange comprises at least one groove, and further wherein said anterior cover comprises at least one tab sized to be received in said at least one groove of said anterior flange.

13. A method according to claim 12 wherein said anterior cover further comprises a lateral protrusion extending laterally from the lateralmost edge of said anterior cover.

14. A method according to claim 13 wherein said lateral protrusion of said anterior cover engages the perimeter of said articulating surface component when said articulating surface component is mounted to said base portion, whereby to lock said articulating surface component to said base portion.

15. A method according to claim 9 wherein said baseplate is secured to the glenoid by at least one base portion screw disposed in said at least one opening in said base portion and by at least one flange screw disposed in said at least one opening in said flange.

16. A method according to claim 9 wherein said laterally-facing surface of said articulating surface component is concave.

17. A method according to claim 9 wherein said laterally-facing surface of said articulating surface component is convex.

18. A method according to claim 9 comprising the further steps of:
   dismounting said anterior cover from said anterior flange;
   dismounting said articulating surface component from said base portion;
   mounting another articulating surface component to said base portion, such that said at least one base portion screw is covered by said another articulating surface component; and
   mounting said anterior cover to said anterior flange, such that said another articulating surface component is locked to said base portion and said at least one flange screw is covered by said anterior cover.

19. A method according to claim 18 wherein said laterally-facing surface of said articulating surface component is concave, and further wherein said laterally-facing surface of said another articulating surface component is convex.

20. A method according to claim 9 comprising the further steps of:
   dismounting said anterior cover from said anterior flange;
   dismounting said articulating surface component from said base portion; and
   dismounting said baseplate from the glenoid.

\* \* \* \* \*